(12) United States Patent
Marchioni

(10) Patent No.: US 6,932,989 B2
(45) Date of Patent: Aug. 23, 2005

(54) THERAPEUTIC COMPOSITION PROVIDING ENHANCED CARDIAC FUNCTION

(76) Inventor: Artista Marchioni, 41 Aspen Way, Rolling Hills Estates, CA (US) 90274

( * ) Notice: Subject to any disclaimer, the term of this patent is extended or adjusted under 35 U.S.C. 154(b) by 89 days.

(21) Appl. No.: 10/652,050

(22) Filed: Aug. 30, 2003

(65) Prior Publication Data

US 2005/0048146 A1 Mar. 3, 2005

(51) Int. Cl.⁷ .............................................. A61K 35/78
(52) U.S. Cl. ..................... 424/756; 424/725; 424/732; 424/760; 424/764; 424/773; 424/777; 514/824
(58) Field of Search ................................. 424/725, 756, 424/732, 760, 764, 773, 777; 514/824

(56) References Cited

U.S. PATENT DOCUMENTS

| | | | | |
|---|---|---|---|---|
| 5,094,782 A | * | 3/1992 | Chen et al. | 554/63 |
| 5,910,308 A | * | 6/1999 | D'Jang | 424/729 |
| 6,054,128 A | * | 4/2000 | Wakat | 424/765 |
| 6,093,404 A | * | 7/2000 | Kattan | 424/732 |
| 6,579,542 B1 | * | 6/2003 | Faulkner | 424/726 |
| 6,599,522 B2 | * | 7/2003 | Mokshagundam, deceased et al. | 424/439 |

FOREIGN PATENT DOCUMENTS

| | | | |
|---|---|---|---|
| CN | 1143518 | * | 2/1997 |
| CN | 1179912 | * | 4/1998 |
| JP | 2001169728 | * | 6/2001 |
| KR | 2001076537 | * | 8/2001 |
| RU | 2090202 | * | 9/1997 |

OTHER PUBLICATIONS

Castleman, M. The Healing Herbs. 1991. Rodale Press, Emmaus, Pennsylvania, pp. 143–146, 186–189, 209–211, 300–304, and 355–357.*

PDR for Herbal Medicines. 1998. Mecical Economics Co., Montvale, New Jersey, pp. 715–717 and 932–933.*

Peirce, A. The American Pharmaceutical Association Practical Guide to Natural Medicines. 1999. Stonesong Press Book. William Morrow and Company, Inc., New York, New York.*

* cited by examiner

Primary Examiner—Christopher R. Tate
(74) Attorney, Agent, or Firm—Karambelas & Associates

(57) ABSTRACT

A herbal therapeutic composition is provided which enhances cardiac function comprising hawthorn berry, turmeric root and cayenne pepper. Other herbal substituents which further enhance this novel composition are disclosed including motherwort, bilberry, fresh dandelion root, and ginger root.

13 Claims, No Drawings

THERAPEUTIC COMPOSITION PROVIDING ENHANCED CARDIAC FUNCTION

I. FIELD OF THE INVENTION

This invention relates to a therapeutic composition comprising naturally occurring herbal substituents which enhance proper cardiac functioning. Heart disease is the leading cause of death for both men and women in the United States. Knowledge regarding the human heart is an aid in prevention of heart disease so that one can live a healthier more active life by learning about the disease and treatments and becoming an active participant in the care applied.

Heart disease is comprehended to include coronary artery distress or hardening of the arteries that provide oxygen and nutrients to the heart; abnormal heart rhythms which are an irregular or abnormal heart beat or arrhythmia; heart failure which means the heart does not pump as well as it should, heart valve disease in which heart valves do not work correctly; congenital heart disease which is a type of defect in one or more structures of the heart or blood vessels that occur before birth; cardiomyopathies which are diseases of the heart muscle itself, and pericarditis which is the inflammation of the lining that surrounds the heart.

The current wisdom proposed by the medical authorities includes quitting smoking, improving cholesterol levels, controlling high blood pressure, getting active, eating right, achieving and maintaining a healthy weight, managing stress and anger, and controlling diabetes.

All of these methods of prevention are arduous, time consuming and many times costly in addition to the methods of treatment when heart disease does occur including extensive medication, which again can be time consuming, expensive and have dangerous side effects. Ultimately life threatening surgery may prove to be necessary.

There is therefore a continuing, demonstrated need to enhance cardiac function using substituents that are therapeutic but have virtually no side effects.

II. OBJECTS OF THE INVENTION

It is therefore an object of the invention to provide a novel therapeutic composition to promote cardiac efficiency.

Still another object of this invention is to provide a novel herbal composition that mitigates cardiac inflammation.

Yet another object of this invention is to provide a herbal composition that enhances cardiac activity.

Yet again another object of this invention is to provide a novel composition of herbal substituents in suitable concentrations to promote natural healthy cardiac activity.

III. SUMMARY OF THE INVENTION

These and other objects of the present invention are accomplished generally speaking by providing a herbal composition that enhances cardiac function and minimizes inflammation of the heart, and more specifically a therapeutic herbal composition comprising hawthorn berry, turmeric root, and cayenne pepper. Hawthorn berry is known to enhance cardiac function, support normal blood pressure through dilation of coronary arteries and inhibit an ACE, an enzyme associated with elevated blood pressure. It enhances oxygen to the heart and blood flow to the extremities. Hawthorn is further known to enhance the function of the entire circulatory system and the health of blood vessels throughout the body consequently strengthening the heart. Turmeric root stimulates bile flow, resulting in improved liver function and reduced cholesterol. It is a stronger antioxidant than Vitamin C or E and may inhibit tumor growth. Turmeric has anti-inflammatory properties and aids in protecting the liver from damaging exposure to drugs, environmental toxins and metabolic byproducts. Cayenne pepper is rich in flavonoids that are known to strengthen and dilate blood vessels and capillaries, creating a powerful increase in circulatory health. Cayenne inhibits cholesterol production by the liver and increases excretion of cholesterol, as well as enhancing absorption and utilization of other herbs and increasing metabolic rate and fat burning.

The novel composition of the instant invention has been found to greatly enhance the body's ability to resist inflammation of the heart and thus enhance cardiac function. This unique combination provides a surprisingly enhanced anti-inflammatory effect on the cardiovascular system. This unique composition may be further enhanced by adding any or all of the following herbal substituents: motherwort herb, bilberry fruit, fresh dandelion root, garlic bulb, and ginger root.

Motherwort herb is known to relax the heart, calm palpitations and regulate blood pressure by relaxing coronary arteries. It is a mild sedative and acts as a tonic for the nervous system, lowering anxiety and stress, and reducing the negative effects of these conditions on the entire system. It is also known to relieve adrenal over-stimulation and reduce overactive thyroid. Bilberry fruit is known to strengthen fragile arteries and capillaries, and improve circulation to extremities, brain, eyes and heart. This benefit relieves varicose veins, reduces blood clots and atherosclerosis and is known to help in preventing strokes, heart attacks and vein problems. Bilberry is a powerful antioxidant that protects against free radical damage. Fresh dandelion root is known to be an effective diuretic with action comparable to many drugs intended for this purpose. However, unlike many harsh pharmaceuticals which aggravate kidney function and create electrolyte imbalance when used, this herb is a valuable tonic which is rich in potassium and other minerals, supports healthy liver function and can be used safely for long periods of time. Garlic bulb is known to control atherosclerosis, cholesterol and blood pressure. Garlic can increase HDL while lowering triglycerides and is known to enhance dilation of blood vessels allowing increased microcirculation to the hands and feet. It also has antioxidant properties that reduce free radical damage to the cells while protecting the liver against the toxic effects of drugs and pollutants. Ginger root is a well known anti-inflammatory which enhances digestion, reduces cholesterol and lowers blood pressure and blood clotting. It is known to increase circulation and provides muscle relaxation and has antispasmodic herb properties.

This composition is provided in a liquid herbal extract form which is absorbed up to 40% better than tablets or capsules. This composition is available as an alcohol free glycerite, eliminating potential concerns with alcohol extracts. The herbs employed are to be certified organically grown or ethically wildharvested, and are never to be fumigated or irradiated. These herbs should be harvested at the peak of activity to maximize potency.

Although each of these substituents in its own right is therapeutic and enhancing to the cardiac function and circulatory system, when combined in this novel composition in any suitable concentration, they are found to be extremely effective in reducing inflammation of the heart and promoting healthy cardiac function.

Although these substituents may be combined in any suitable ratio, it is found preferable to combine them in the following parts by weight: 4 to 8 parts by weight hawthorn berry, 2 to 6 parts of fresh dandelion root by weight, ½ to 4 parts garlic bulb, 1 to 5 parts motherwort herb, about 0.5 to 3½ parts by weight bilberry, ½ to 3½ parts fresh turmeric root, ¼ to 2 fresh ginger root and 0.05 to 0.4 cayenne fruit.

Although the three herbal substituent unique therapeutic composition of the instant invention may have its substituents combined in any suitable ratio, it is found preferable to employ the following composition: hawthorn berry about 6 parts by weight, turmeric root about 2 parts by weight, and cayenne pepper about 0.2 part by weight. Any suitable weight range may be employed for the three substituent herbal composition of the instant invention. Typical compositions of the three substituents include hawthorn berry in a range of about 60–80% by weight; turmeric root in a range of about 14–34% by weight; and cayenne pepper in a range of about 0.05–0.3% by weight. Optimal results have been obtained when employing the following composition of the three substituent herbal composition: hawthorn berry at about 73% by weight, turmeric root at about 24% by weight, and cayenne pepper at about 3% by weight.

Further exemplary compositions in suitable concentrations are obtained when further including motherwort herbal substituent as follows: hawthorn berry in a range of about 40–60% by weight, turmeric root in a range of about 10–30% by weight, cayenne pepper in a range of about 1–3% by weight, and motherwort in a range of about 20–30% by weight.

When bilberry is employed to provide a five substituent herbal composition, a preferred composition is as follows: hawthorn berry at about 6 parts by weight, turmeric root at about 2 parts by weight, cayenne pepper at about 0.2 part by weight, motherwort at about 3 parts by weight, and bilberry at about 2 parts by weight. Typical concentrations of this five substituent herbal composition include: hawthorn berry in a range of about 35–55% by weight, turmeric root in a range of about 10–20% by weight, cayenne pepper in a range of about 0.75–2.25% by weight, motherwort in a range of about 10–30% by weight, and bilberry in a range of about 10–20% by weight. Optimal results may be achieved by employing this five substituent herbal composition in the following concentrations: hawthorn berry at about 45% by weight, turmeric root at about 15% by weight, cayenne pepper at about 1½% by weight, motherwort at about 23% by weight, and bilberry at about 15% by weight.

A six substituent herbal composition by adding fresh dandelion root would typically comprise: hawthorn berry at about 6 parts by weight, turmeric root at about 2 parts by weight, cayenne pepper at about 0.2 part by weight, motherwort at about 3 parts by weight, bilberry at about 2 parts by weight, and fresh dandelion root at about 4½ parts by weight. Typical ranges employed in a six substituent herbal composition would include about 20–40% by weight hawthorn berry, about 5–15% by weight turmeric root, about ½–1½% by weight cayenne pepper, about 10–20% by weight motherwort, about 5–15% by weight bilberry, about 15–35% by weight fresh dandelion root.

A further enhanced seven substituent herbal composition may be employed adding ginger root at the following compositions: hawthorn berry at about 6 parts by weight, turmeric root at about 2 parts by weight, cayenne pepper at about 0.2 part by weight, motherwort at about 3 parts by weight, bilberry at about 2 parts by weight, fresh dandelion root at about 4½ parts by weight, and ginger root at about 1 part by weight. Typical composition ranges of this composition include: hawthorn berry in a range of about 20–40% by weight, turmeric root in a range of about 5–15% by weight, cayenne pepper in a range of about 0.5–1.5% by weight, motherwort in a range of about 10–20% by weight, bilberry in a range of about 5–15% by weight, fresh dandelion root in a range of about 15–35% by weight, and ginger root in a range of about 3–7% by weight. Optimal results of a seven substituent herbal composition may be obtained by employing the following composition: hawthorn berry at about 32% by weight, turmeric root at about 11% by weight, cayenne pepper at about 1% by weight, motherwort at about 16% by weight, bilberry at about 10% by weight, fresh dandelion root at about 24% by weight, and ginger root at about 5% by weight.

Any suitable solvent may be employed in providing the solutions of the respective herbal substituents. Typical solvents include water, alcohol, so forth.

Any suitable extraction may be employed to provide the substituents of the instant invention. Typical methods of extraction include alcohol, water, solvent extraction, among others.

While the present invention has been particularly described with respect to certain substituent elements in its preferred embodiment, it will be understood that the invention is not limited to these particular substituents described in the preferred embodiments, or the sequence in adding substituents. On the contrary, it is intended to cover all alternatives, modifications, and equivalents as may be included within the spirit and scope of the invention defined by the appended claims.

In addition, other substituents may be employed in the compositions of the instant invention as claimed with similar results. In particular, the scope of the invention is intended to include, for example, those substituents which further enhance the taste, solubility and appearance of these compositions, in addition to other substituents which provide further synergy to these herbal compositions.

What is claimed is:

1. A herbal composition that enhances cardiac function and minimizes inflammation of the heart comprising effective amounts of hawthorn berry, turmeric root and cayenne pepper.

2. The composition as defined in claim 1 wherein said hawthorn berry is present in a range of about 60–80%, said turmeric root is present in a range of about 14–34%, and said cayenne pepper is present in a range of about 0.05–3% by weight.

3. The composition as defined in claim 1 wherein said hawthorn berry is present in a weight percentage of about 73%, said turmeric root is present in a weight percentage of about 24%, and said cayenne pepper is present in a weight of about 3%.

4. The composition as defined in claim 1 further comprising motherwort herbal substituent.

5. The composition as defined in claim 4 wherein said hawthorn berry is present in a weight percentage of about 40–60%, said turmeric root is present in a weight percentage of about 10–30%, said cayenne pepper is present in a range of about 1–3%, and said motherwort is present in a weight percentage of about 20–30%.

6. The composition as defined in claim 4 further comprising bilberry herbal substituent.

7. The composition as defined in claim 6 wherein said hawthorn berry is present in a weight percentage of about 35–55%, said turmeric root is present in a weight percentage of about 10–20%, said cayenne pepper is present in a weight percentage of about 0.75–2.25%, said motherwort is present in a weight percentage of about 10–30%, and said bilberry is present in a weight percentage of about 10–20%.

8. The composition as defined in claim 6 further comprising fresh dandelion root.

9. The composition as defined in claim 8 wherein said hawthorn berry is present in a range of about 20–40%, said turmeric root is present in a range of about 5–15%, said cayenne pepper is present in a range of about 0.05–2%, said motherwort is present in a range of about 10–30%, said bilberry is present in range of about 5–20%, and said dandelion root is present in a range of about 15–35%.

10. The composition as defined in claim 8 further comprising the herbal substituent ginger root.

11. The composition as defined in claim 10 wherein said hawthorn is present in a range of about 15–40%, said turmeric root is present in a range of about 5–15%, said cayenne pepper is present in a range of about 0.05–1.5%, said motherwort is present in a range of about 5–20%, said bilberry is present in a range of about 5–15%, said dandelion root is present in a range of about 15–40%, and said ginger root is present in a range of about 3–8% by weight.

12. A herbal composition that enhances cardiac function and minimizes inflammation of the heart comprising about 4–8 parts by weight hawthorn berry, about 2–6 parts by weight fresh dandelion root, about 0.5–4 parts by weight garlic bulb; about 1–5 parts by weight motherwort herb; from about 0.5–3½ parts by weight bilberry; from about 0.5–3½ parts by weight fresh turmeric root; from about 0.25–2 parts by weight fresh ginger root; and from about 0.05–0.4 parts by weight cayenne pepper.

13. A herbal composition that enhances cardiac function and minimized inflammation of the heart comprising hawthorn berry at about 6 parts by weight; fresh dandelion root at about 4½ parts by weight; garlic bulb at about 2½ parts by weight; motherwort herb at about 3 parts by weight; bilberry root at about 2 parts by weight; fresh turmeric root at about 2 parts by weight; fresh ginger root at about 1 part by weight; and cayenne fruit at about 0.2 part by weight.

* * * * *